United States Patent [19]

Bertram et al.

[11] Patent Number: 5,201,936
[45] Date of Patent: Apr. 13, 1993

[54] SUBSTITUTED THIENO[3,2-B]PYRAN-5,7-DIONES

[75] Inventors: Heinz-Jürgen Bertram, Holzminden; Klaus Lürssen, Bergisch Gladbach; Hans-Joachim Santel, Leverkusen; Robert R. Schmidt, Bergisch Gladbach; Andrew Plant, Odenthal-Steinhaus; Bernd-Wieland Krüger, Bergisch Gladbach; Achim Harder, Cologne; Norbert Mencke, Leverkusen, all of Fed. Rep. of Germany

[73] Assignee: Bayer Aktiengesellschaft, Leverkusen, Fed. Rep. of Germany

[21] Appl. No.: 777,878

[22] Filed: Oct. 15, 1991

[30] Foreign Application Priority Data

Oct. 25, 1990 [DE] Fed. Rep. of Germany ....... 4033904
Apr. 10, 1991 [DE] Fed. Rep. of Germany ....... 4111652

[51] Int. Cl.$^5$ .................... A01N 43/32; A61K 31/38; C07D 497/04
[52] U.S. Cl. ................................ 504/289; 549/50; 514/443; 504/191; 504/166
[58] Field of Search .................. 71/90; 549/50, 285; 514/443

[56] References Cited

FOREIGN PATENT DOCUMENTS 0241834 10/1987 European Pat. Off. .
0345635 12/1989 European Pat. Off. .
411419 2/1991 European Pat. Off. .............. 549/50
1964803 7/1970 Fed. Rep. of Germany .
3701298 7/1988 Fed. Rep. of Germany .
896456 2/1945 France .
8804652 6/1988 PCT Int'l Appl. .

OTHER PUBLICATIONS

T. Kralt, *Recueil,* "Anticoagulants," 86, pp. 971–974 (1967).
F. Duus, *Tetrahedron,*" The Influence of Substituents on Preparation and Tautomerism of Open–Chain β--Thioketoesters," 28, pp. 5923–5947 (1972).

*Primary Examiner*—Richard L. Raymond
*Assistant Examiner*—M. W. Russell
*Attorney, Agent, or Firm*—Sprung Horn Kramer & Woods

[57] ABSTRACT

Novel substituted thieno[3,2-b]pyran-5,7-diones of the general formula (I)

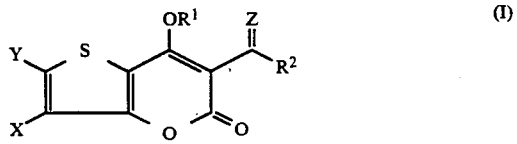

Processes for their preparation and their use as herbicides and as plant growth regulators and novel intermediates of the formula (VI)

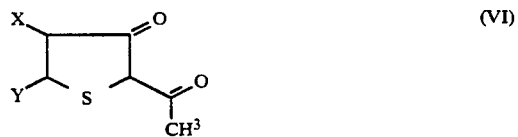

(in which $R^1$, $R^2$, X, Y and Z have the meaning given in the description).

6 Claims, No Drawings

SUBSTITUTED THIENO[3,2-B]PYRAN-5,7-DIONES

The present invention relates to novel, substituted thieno [3,2-b]pyran-5,7-diones to processes and novel intermediates for their preparation, and to their use as endoparasiticides, herbicides and as plant growth regulators.

It has been disclosed that certain tetrahydropyran-2,4-diones have herbicidal properties (cf. EP-A-0,345,635).

Novel substituted thieno[3,2-b]pyran-5,7-diones of the general formula (I) and of their tautomeric forms

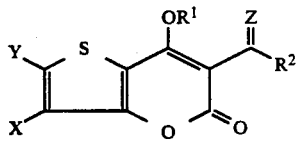

have now been found, in which $R^1$ represents hydrogen, straight-chain or branched radicals from the series comprising alkyl, alkenyl, alkynyl alkylsulphonyl, alkylcarbonyl, alkenylcarbonyl, in each case substituted or unsubstituted phenyl, benzoyl or benzenesulphonyl, $R^2$ represents straight-chain or branched radicals from the series comprising alkyl, alkenyl, alkynyl, halogenoalkyl, cycloalkyl, in each case substituted or unsubstituted phenyl or benzyl, X and Y independently of one another represent hydrogen, halogen, cyano, nitro, straight-chain or branched alkyl, alkenyl, alkynyl, halogenoalkyl, cycloalkyl, alkylcarbonyl, alkoxycarbonyl, alkyloxy, alkylthio, halogenoalkoxy, halogenoalkylthio, alkylamino, dialkylamino, in each case substituted or unsubstituted aryl, aralkyl, aryloxy or arylthio, or X and Y together with the adjoining C atoms form a carbocyclic ring which is optionally interrupted by hetero atoms and Z represents oxygen or =NOR³, where $R^3$ represents hydrogen and straight-chain or branched radicals from the series comprising alkyl, alkenyl, alkynyl, halogenoalkyl, halogenoalkenyl, halogenoalkynyl, cycloalkyl, substituted or unsubstituted phenyl, phenylalkyl, and their tolerated salts are possible.

Furthermore, it has been found that the novel thieno[3,2-b]pyran-5,7-diones of the general formula (I) and their tautomeric forms

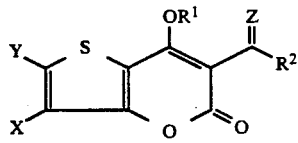

in which $R^1$ represents hydrogen, straight-chain or branched radicals from the series comprising alkyl, alkenyl, alkynyl alkylsulphonyl, alkylcarbonyl, alkenylcarbonyl, in each case substituted or unsubstituted phenyl, benzoyl or benzenesulphonyl, $R^2$ represents straight-chain or branched radicals from the series comprising alkyl, alkenyl, alkynyl, halogenoalkyl, cycloalkyl, in each case substituted or unsubstituted phenyl or benzyl, X and Y independently of one another represent hydrogen, halogen, cyano, nitro, straight-chain or branched alkyl, alkenyl, alkynyl, halogenoalkyl, cycloalkyl, alkylcarbonyl, alkoxycarbonyl, alkyloxy, alkylthio, halogenoalkoxy, halogenoalkylthio, alkylamino, dialkylamino, in each case substituted or unsubstituted aryl, aralkyl, aryloxy or arylthio, or X and Y together with the adjoining C atoms form a carbocyclic ring which is optionally interrupted by hetero atoms and Z represents oxygen or NOR³, where $R^3$ represents hydrogen and straight-chain or branched radicals from the series comprising alkyl, alkenyl, alkynyl, halogenoalkyl, halogenoalkenyl, halogenoalkynyl, cycloalkyl, substituted or unsubstituted phenyl or phenylalkyl, and their tolerated salts are obtained when a) Thieno[3,2-b]pyran-5,7-diones of the formula (II)

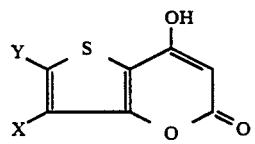

in which

X and Y have the abovementioned meaning, are reacted with an acid chloride of the formula (III)

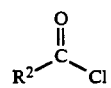

in which $R^2$ has the abovementioned meaning, if appropriate in the presence of a base and if appropriate in the presence of a diluent to give the enol ester and the product is subsequently reacted in the same or in another diluent at a temperature between 0° C. and 100° C., to give the C-acylated product if appropriate in the presence of a reaction auxiliary, or b) when the thienopyran-2,4-diones of the general formula (II) are reacted with a carboxylic acid of the general formula (IV)

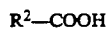

$$R^2\text{—COOH} \qquad \text{(IV)}$$

in which $R^2$ has the abovementioned meaning, if appropriate in the presence of a diluent and if appropriate in the presence of a dehydrating reagent and if appropriate in the presence of a reaction auxiliary, at a temperature between 0° C. and 100° C., or c) when thieno[3,2-b]pyran-5,7-diones of the formula (II) are reacted with an acid chloride of the formula (III), if appropriate in the presence of a Lewis acid, to give derivatives of the general formula (I) in which t represents oxygen and $R^1$ represents hydrogen in a single step, d) or when, in the case where Z represents =NOR³ in formula (I) thieno-[3,2-b]pyran-5,7-diones of the formula (I)

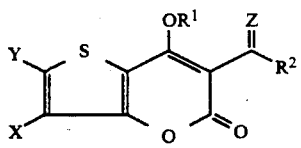

in which

Z represents oxygen and the remaining radicals have the abovementioned meaning, are reacted with a corresponding hydroxylamine or its ammonium compounds $R^3ONH_2$ and $R^3ONH_3^{\oplus}W^{\ominus}$ respectively, wherein $W^{\ominus}$ represents an anion equivalent of an inorganic acid and $R^3$ has the abovementioned meaning, at a temperature between 0° C. and 80° C., those thieno [3,2-b]pyran-5,7-dione derivatives of the formula (I) in which Z denotes an oxime ether group (=NOR³) being obtained.

The compounds of the formula (I) in which
$R^1$ represents straight-chain or branched radicals from the series comprising alkyl, alkenyl, alkynyl, alkylsulphonyl, alkylcarbonyl, alkenylcarbonyl, in each case substituted or unsubstituted phenyl, benzenesulphonyl or benzoyl,
and $R^2$, X, Y, and Z have the above mentioned meaning, are obtained in a following reaction step if the compounds of the formula (I) in which
$R^1$ represents hydrogen are reacted with compounds of the formula (IX)

$$R^1—V \quad (IX)$$

in which
$R^1$ represents straight-chain or branched radicals from the series alkyl, alkenyl, alkynyl, alkylsulphonyl, alkylcarbonyl, alkenylcarbonyl, in each case substituted or unsubstituted phenyl, benzenesulphonyl or benzoyl, and V represents halogen, especially chlorine, bromine or iodine (process e).

The compounds of the formula (I) are highly suitable for use as endoparasiticides, in particular in the field of veterinary medicine.

Finally, it has been found that the novel thieno [3,2-b]pyran-5,7-diones of the general formula (I) in which Z denotes an oxime ether group (=NOR³), have an unexpected herbicidal action, and derivatives in which Z denotes oxygen have plant-growth-regulating properties.

The invention preferably relates to compounds of the formula (I) and their tautomeric forms in which
$R^1$ represents hydrogen, straight-chain or branched radicals from the series comprising $C_1-C_7$-alkyl, $C_3-C_6$-alkenyl, $C_3-C_6$-alkynyl, $C_1-C_6$-alkylsulphonyl, $C_1-C_6$-alkylcarbonyl, $C_1-C_6$-alkenylcarbonyl, in each case substituted or unsubstituted phenyl, benzenesulphonyl or benzoyl, $R^2$ represents straight-chain or branched radicals from the series comprising $C_1-C_7$-alkyl, $C_2-C_6$-alkenyl, $C_2-C_6$-alkynyl, $C_1-C_7$-halogenoalkyl having 1 to 15 identical or different halogen atoms, $C_3-C_7$-cycloalkyl or in each case substituted or unsubstituted phenyl or benzyl, X and Y independently of one another represent hydrogen, halogen, cyano, nitro, straight-chain or branched $C_1-C_7$-alkyl, $C_2-C_6$-alkenyl, $C_2-C_6$-alkynyl, $C_1-C_7$-halogenoalkyl having 1 to 15 identical or different halogen atoms, $C_3-C_6$-cycloalkyl, $C_1-C_6$-alkylcarbonyl, $C_1-C_6$-alkyloxycarbonyl, $C_1-C_7$-alkyloxy, $C_1-C_7$-alkythio, 1-5 halogeno-$C_{1-4}$-alkoxy, 1-5 halogeno-$C_{1-4}$-alkythio, $C_1-C_7$-alkylamino, $C_1-C_7$-dialkylamino, in each case substituted or unsubstituted aryl, aralkyl, aryloxy or arylthio, or X and Y together form a carbocyclic ring which consists of 4 to 8 carbon atoms and which is optionally interrupted by hetero atoms such as nitrogen, oxygen or sulphur, and Z represents oxygen or NOR³, where
$R^3$ represents hydrogen and straight-chain or branched radicals from the series comprising $C_1-C_7$-alkyl, $C_2-C_6$-alkenyl, $C_2-C_6$-alkynyl, $C_1-C_7$-halogenoalkyl having 1 to 15 identical or different halogen atoms, $C_2-C_6$-halogenoalkenyl having 1 to 11 identical or different halogen atoms, $C_2-C_6$-halogenoalkynyl having 1 to 9 identical or different halogen atoms, $C_3-C_6$-cycloalkyl, or substituted or unsubstituted phenyl or benzyl, suitable substituents on the aromatic radicals being halogen, cyano, nitro, straight-chain or branched alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphonyl, alkylenedioxy, halogenoalkylenedioxy, and their tolerated salts.

Particularly preferably, the invention relates to compounds of the formula (I) and their tautomeric forms in which
$R^1$ represents hydrogen, straight-chain or branched and radicals from the series comprising $C_1-C_6$-alkyl, $C_3-C_4$-alkenyl, $C_2-C_4$-alkynyl, $C_1-C_4$-alkylsulphonyl, $C_1-C_4$-alkylcarbonyl, $C_2-C_5$-alkenylcarbonyl, or in each case substituted or unsubstituted phenyl, benzenesulphonyl or benzoyl, $R^2$ represents straight-chain or branched radicals from the series comprising $C_1-C_6$-alkyl, $C_1-C_4$-alkenyl, $C_2-C_4$-alkynyl, $C_1-C_6$-halogenoalkyl having 1 to 13 identical or different halogen atoms or $C_3-C_6$-cycloalkyl, in each case substituted or unsubstituted phenyl or benzyl X and Y independently of one another represent hydrogen, halogen, cyano, nitro, straight-chain or branched $C_1-C_6$-alkyl, $C_2-C_5$-alkenyl, $C_2-C_5$-alkynyl, $C_1-C_6$-halogenoalkyl having 1 to 13 identical or different halogen atoms, $C_3-C_6$-cycloalkyl, $C_3-C_6$-alkylcarbonyl, $C_1-C_6$-alkyloxycarbonyl, $C_1-C_6$-alkyloxy, $C_1-C_6$-alkylthio, $C_1-C_6$-alkylamino, $C_1-C_6$-dialkylamino, in each case substituted or unsubstituted aryl, aralkyl, aryloxy or arylthio, or X and Y together with the adjoining C atoms form a carbocyclic ring which consists of 4 to 8 carbon atoms and which is optionally interrupted by hetero atoms such as nitrogen, oxygen or sulphur, and Z represents oxygen or NOR³, where
$R^3$ represents hydrogen and straight-chain or branched radicals from the series comprising $C_1-C_6$-alkyl, $C_2-C_4$-alkenyl, $C_2-C_4$-alkynyl, $C_1-C_6$-halogenoalkyl having 1 to 13 identical or different halogen atoms, $C_2-C_4$-halogenoalkenyl having 1 to 7 identical or different halogen atoms, $C_2-C_4$-halogenoalkynyl having 1 to 5 identical or different halogen atoms, $C_3$-$C_6$-cycloalkyl, or substituted or unsubstituted phenyl or benzyl, suitable substituents on the aromatic radicals being halogen, cyano, nitro, straight-chain or branched $C_1$-$C_4$-alkyl, 1-5-halogeno-$C_{1-4}$-alkyl-$C_{1-4}$alkoxy, 1-5-halogeno-$C_{1-4}$-alkoxy, $C_{1-4}$-alkylthio, 1-5-halogeno-$C_{1-4}$-alkylthio, $C_{1-4}$-alkylsulphinyl, 1-5-halogeno-$C_{1-4}$-alkylsulphinyl, $C_{1-4}$-alkylsulphonyl, 1-5-halogeno-$C_{1-4}$-alkylsulphonyl, $C_{1-2}$-alkylenedioxy, 1-4-halogeno-$C_{1-2}$-alkylenedioxy, and their tolerated salts with monovalent and divalent metal cations, in each case substituted or unsubstituted ammonium ions, phosphonium ions, sulphonium ions and sulphoxonium ions.

The invention particularly preferably relates to compounds of the formula (I) and their tautomeric forms in which $R^1$ represents hydrogen, methyl, ethyl, n-propyl, i-propyl, n-butyl, i-butyl, t-butyl, n-pentyl, i-pentyl, allyl, n-butenyl, i-butenyl, propinyl, acetyl, propionyl, acroyl, isobutyryl, pivaloyl, valeroyl, phenyl, benzoyl, 4-methylbenzoyl, 4-ethylbenzoyl, 4-n-propylbenzo-yl, 4-isopropylbenzoyl, 4-n-butyl-benzoyl, 4-i-butylbenzoyl, 4-t-butylbenzoyl, 2,4,6-trimethylbenzoyl, p-methylphenylsulphonyl, benzenesulphonyl, $R^2$ represents methyl, ethyl, n-propyl, i-propyl, n-butyl, s-butyl, i-butyl, t-butyl, n-pentyl, i-pentyl, s-pentyl, t-pentyl, neo-pentyl, n-hexyl, cyclopropyl, cyclobutyl, cyclopentyl, cyclohexyl, in each case substituted or unsubstituted phenyl or benzyl, X and Y independently of one another represent hydrogen, fluorine, chlorine, bromine, cyano, methyl, ethyl, n-propyl, isopropyl, n-butyl, i-butyl, s-butyl, t-butyl, n-pentyl, cyclopropyl, cyclobutyl, cyclopentyl, cyclohexyl, methoxy, ethoxy, n-propyloxy, i-propyloxy, n-butyloxy-, i-butyloxy, t-butyloxy, n-pentyloxy or neo-pentyloxy, methylthio-, ethylthio-, n-propylthio, i-propylthio, n-butylthio-, i-butylthio, t-butylthio, n-pentylthio, dimethylamino, diethylamino, dipropylamino, dibutylamino, methoxymethyl, ethoxymethyl, methylthiomethyl, ethylthiomethyl, 1-methoxyethyl, 2-methoxyethyl, 1,3-dimethoxypropyl, 2-ethoxy-ethyl, 1-methyl-2-methylthio-ethyl, 2-methyl-1-methylthiomethylpropyl, 1-methyl-butyl, 2-methyl-1-propenyl, phenyl, 4-methylphenyl, 4-trifluoromethylphenyl, 2,4-dichlorophenyl, 4-methoxyphenyl, 2,4,6-trimethylphenyl, 3,5-dibromophenyl, 4-methylthiophenyl, 4-fluorophenyl, or X and Y together with the adjoining C atoms form a carbocyclic ring which consists of 5 to 6 carbon atoms and which is optionally interrupted by heteroatoms such as nitrogen, oxygen or sulphur, and Z represents oxygen or $NOR^3$, where $R^3$ represents hydrogen, methyl, ethyl, n-propyl, i-propyl, n-butyl, i-butyl, t-butyl, allyl, prop-2-ynyl, 3-fluoropropyl, trans-3-chloro-prop-2-enyl, trans-but-2-enyl, cis-3-chloro-prop-2-enyl, but-2-ynyl, 2-methoxyethyl, E-4(4-fluorophenyl)but-2-enyl, E-4(4-chlorophenyl)but-2-enyl, E-4(4-tert.-butylphenyl)but-2-enyl, E-4(4-trifluorophenyl)but-2-enyl; E-4-phenyl-but-2-enyl, 2-thienyl, 3-thienyl; 5-chloro-thienyl or optionally substituted benzyl, suitable substituents on the aromatic radicals being halogen, cyano, nitro, methyl, ethyl, n-propyl, i-propyl, n-butyl, i-butyl, t-butyl, chloromethyl, fluoromethyl, dichloromethyl, trichloromethyl, difluoromethyl, trifluoromethyl, trifluoromethoxy, trifluoromethylthio, methylsulphinyl, methylsulphonyl, trifluoromethylsulphinyl, trifluoromethylsulphonyl, and their tolerated salts for example with monovalent metal cations, in particular sodium, potassium, or an equivalent of a polyvalent cation, for example an alkaline earth metal cation, in particular magnesium, calcium and also agriculturally utilised cations such as manganese, copper, zinc and iron cations, and also ammonium, phosphonium, sulphonium and sulphoxonium cations such as ammonium, tetraalkylammonium, benzyltrialkylammonium, trialkylsulphonium or trialkylsulphoxonium.

The abovementioned definitions of radicals, or illustrations, which are general or mentioned in ranges of preference, apply correspondingly to end products and to the starting materials and intermediates. These definitions of radicals can be combined with each other as desired, but that is to say also between the particular ranges of preference.

If, for example, thieno-[3,2 -b]pyran-5,7-dione and butyry chloride are used as educts, the course of the reaction of process (a) according to the invention can be outlined by the following equation:

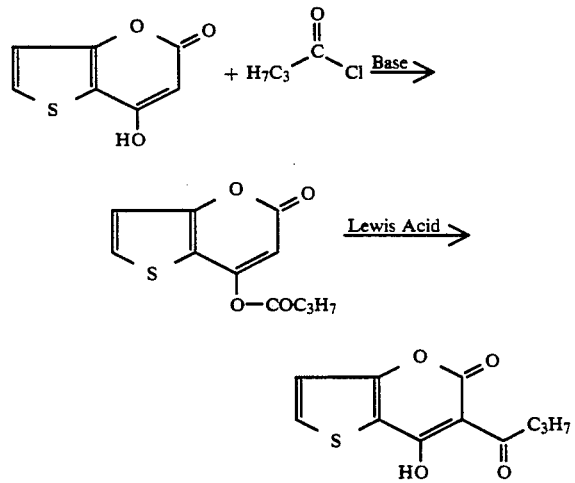

In this process, the thieno-[3,2-b]pyran-5,7-dione first reacts to give the enol ester and the product subsequently reacts, with an acid or basic catalyst, in the same or in a different solvent, to give the thieno[3,2-b]-6-butyryl-pyran-5,7-dione according to the invention.

In the presence of a Lewis acid catalyst thieno[3,2-b]-6-butyryl-pyran-5,7-dione is obtained in a single reaction step according to the invention (process c).

If, for example, thieno-[3,2-b]pyran-5,7-dione and butyric acid are used as educts, the course of the reaction of process (b) according to the invention can be outlined by the following equation:

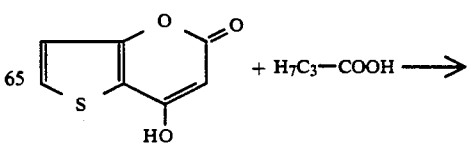

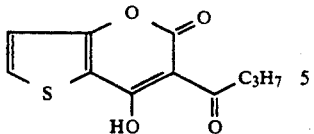

In this case, the thieno[3,2-b]pyran-5,7-dione reacts with the carboxylic acid in question in the presence of a dehydrating reagent such as, for example, inorganic acid chlorides, and in the presence of a catalyst, to give the thieno [3,2-b]pyran-5,7-dione according to the invention.

If, for example, thieno[3,2-b]-6-butyryl-pyran-5,7-dione having a carbonyl group in the side chain and hydroxylamine or its ammonium compound such as ethoxyamine hydrochloride are used as educts, the course of the reaction of process (d) according to the invention can be outline by the following equation:

Formula (II) provides a general definition of the thieno-[3,2-b]pyran-5,7-diones required as educts for carrying out processes (a), (b) and (c) according to the invention. In this formula (II), $R^1$, X and Y preferably represent those radicals which have already been mentioned in connection with the description of the substances of the formula (I) according to the invention as being preferred for these substituents. The thieno[3,2-b]pyran-5,7-diones of the formula (II) are known or can be prepared from 2-acetyl-3-hydroxythiophenes (V) by pro-

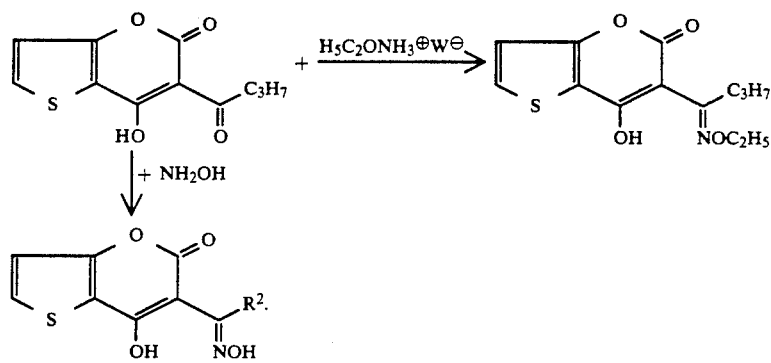

If 8-methyl-thione[3,2-b]-6-(1-ethoxyiminopropyl)-pyran-5,7-dione and iodomethane are used as educts the course of the reaction of process (e) according to the invention can be outlined by the following equation:

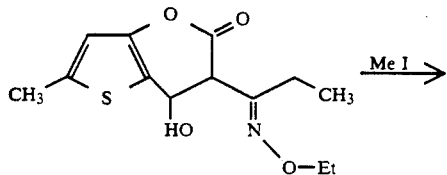

cesses known per se. [T. Kraft, Recueil 86, 971 (1967)].

The 2-acetyl-3-hydroxythiophenes (V) can be successfully synthesised by reacting 2,5-dihydroxy-2,5-dimethyl-1,4-dithiane with propiol esters (cf. T. Kraft, Recueil 86, 971 (1967)) or by reacting 2,5-dihydroxy-2,5-dimethyl-1,4-dithiane with α-halogenoacrylic esters.

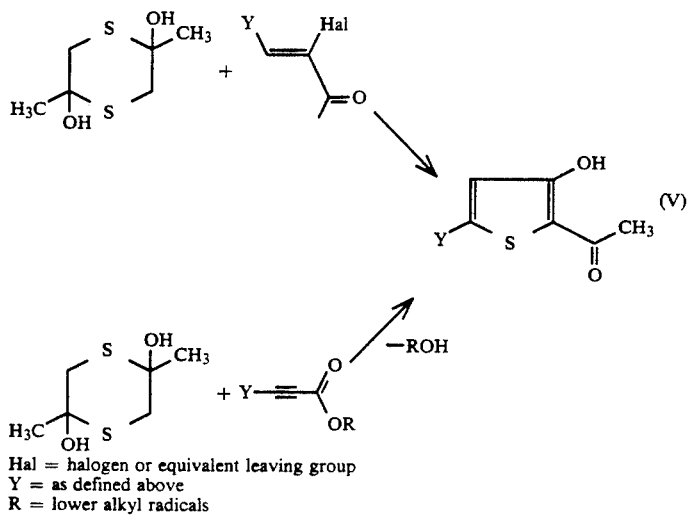

Hal = halogen or equivalent leaving group
Y = as defined above
R = lower alkyl radicals Alternatively, it is also possible to synthesise 2-acetyl-3-hydroxy-thiophenes by reacting β-halogen-substituted α,β-unsaturated esters with 2,5-dihydroxy-2,5-dimethyl-1,4-dithione or by reacting β-thioxo esters with α-halogenoacetone (DE 3,925,719, 1989) or by dehydrogenation of 2-acetyl-3-keto-4,5-dihydrothiophene of the formula (VI) (DE 2,615,885, 1976).

ing out process (b) according to the invention. In these formulae (III) and (IV), $R^2$ preferably represents those radicals which have already been mentioned in connection with the description of the substances of the formula (I) according to the invention as being preferred for this substituent. The acid halides of the formula (III) and the carboxylic acids of the formula (IV) are gener-

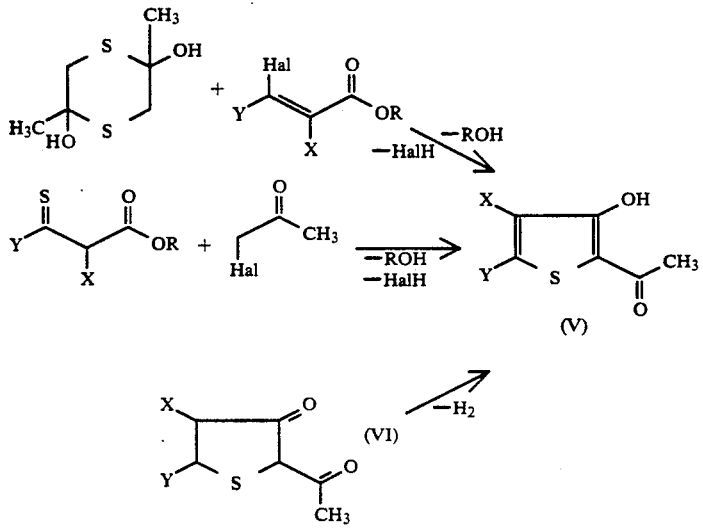

Hal = halogen or equivalent leaving group
X, Y = as defined above

The β-thioxo esters are known [F. Duus, Tetrahedron 28, 5923 (1972)].

The 2-acetyl-3-keto-4,5-dihydrothiophenes of the formula (VI)

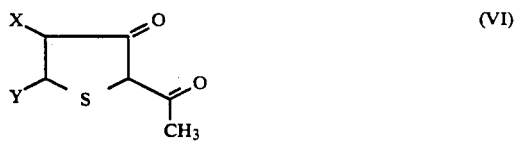

are new and also a subject of the invention. They can be obtained by reacting 2,5-dihydroxy-2,5-dimethyl-1,4-dithiane with acrylic esters of the formula (VII):

ally known compounds of organic chemistry.

Formula (IX) provides a general definition of the organo-halogen compounds furthermore required as educts for carrying out process (e).

In this formula $R^1$ represents those residues except hydrogen, which have been mentioned in connection with the description of the substances of the formula (I) according to the invention as being preferred for $R^2$.

The compounds of the formula (IX) are generally known compounds in organic chemistry.

Formula (I) provides a general definition of the thieno-[3,2-b]pyran-5,7-diones required as educts for carrying out process (c) according to the invention. In this formula (I), $R^1$, $R^2$, X and Y preferably represent those radicals which have already been mentioned in connec-

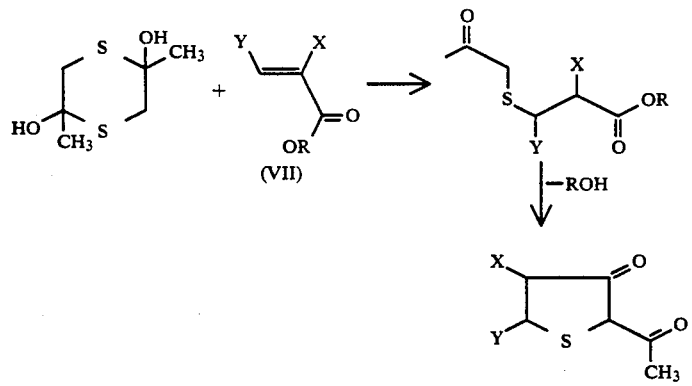

Formula (III) provides a general definition of the acid chlorides furthermore required as educts for carrying out processes (a) and (c) according to the invention, and formula (IV) provides a general definition of the carboxylic acids furthermore required as educts for carrying out tion with the description of the substances of the formula (I) according to the invention as being preferred for these substituents. However, in the case of process (d) according to the invention Z represents an oxime ether group (=NOR³) in which R³ preferably represents those radicals which have also already been mentioned in connection with the description of the substances of the formula (I) according to the invention as being preferred for these substituents:

The compounds of the formula (I) in which R¹ is hydrogen can occur in several tautomeric forms which differ from the formula (I) and which are also part of the invention.

In the event that olefinically unsaturated substituents are present, E and Z isomers can occur in a known fashion and are equally part of the invention.

Suitable diluents for carrying out the processes (a), (b), (c) and (e) according to the invention are inert organic solvents. These include, in particular, aliphatic, alicyclic or aromatic hydrocarbons such as, for example, benzene, toluene, xylene, petroleum ether, hexane, cyclohexane, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, N-methylformanilide, N-methylpyrrolidone or hexamethylphosphoric triamide, esters such as ethyl acetate, or sulphoxides such as dimethyl sulphoxide, or sulphones such as sulpholane, alcohols such as methanol, ethanol or isopropanol, or chlorinated hydrocarbons such as chloroform or dichloromethane.

Processes (a), (b) and (e) according to the invention are preferably carried out in the presence of a suitable reaction auxiliary. Suitable reaction auxiliaries are all inorganic and organic bases which can customarily be used. The following are preferably used: hydrides, hydroxides, amides, alcoholates, carbonates or hydrogen carbonates of alkali metals such as, for example, sodium hydride, sodium amide, sodium hydroxide, sodium methylate, sodium ethylate, potassium t-butylate, sodium carbonate or sodium hydrogencarbonate, and also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU), oxides of alkaline earth metals such as magnesium oxide or calcium oxide.

The base is added in a stoichiometric amount or in an excess.

Examples which may be mentioned of acidic or basic catalysts for process (a), (c) and (e) according to the invention are aluminum chloride, zinc chloride, zinc acetate, trifluoromethylsulphonic acid, tin tetrachloride, 4-dimethyl-aminopyridine and 4-pyrrolidinopyridine.

When carrying out processes (a), (b) and (c) according to the invention, the reaction temperatures can be varied within a substantial range. In general, the processes are carried out at temperatures between −20° C. and 150° C., preferably at temperatures between 0° C. and 100° C., very particularly preferably at temperatures between 20° C. and 80° C.

For carrying out process (a), (b) and (c) according to the invention, 0.8 to 2.5 mol, preferably 1.0 to 1.5 mol, of acid chloride of the formula (III) or 1.0 to 1.5 mol of carboxylic acid of the formula (IV) (process (b)) and, if appropriate, 0.8 to 2.5 mol, preferably 1.0 to 1.5 mol, of reaction auxiliary are generally employed per mole of thieno[3,2-b]pyran-5,7-dione of the formula (II).

The reaction is carried out and the reaction products are worked up and isolated by generally customary methods (cf. also the Preparation Examples).

Suitable diluents for carrying out process (d) according to the invention are inert organic solvents. These include, in particular, aliphatic, alicyclic or aromatic hydrocarbons such as, for example, benzene, toluene, xylene, petroleum ether, hexane, cyclohexane, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides such as dimethylformamide, dimethylacetamide, n-methylformanilide, N-methylpyrrolidone or hexamethylphosphoric triamide, esters such as ethyl acetate, or sulphoxides such as dimethyl sulphoxide, or sulphones such as sulpholane, alcohols such as methanol, ethanol or isopropanol, chlorinated hydrocarbons such as chloroform or dichloromethane.

Process (d) according to the invention is preferably carried out in the presence of a suitable reaction auxiliary. Suitable reaction auxiliaries are all inorganic and organic bases which can customarily be used. The following are preferably used: hydrides, hydroxides, amides, alcoholates, carbonates or hydrogencarbonates of alkali metals such as, for example, sodium hydride, sodium amide, sodium hydroxide, sodium methylate, sodium ethylate, potassium t-butylate, sodium carbonate or sodium hydrogencarbonate, and also tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU), oxides of alkali earth metals such as magnesium oxide or calcium oxide.

The base is added in a stoichiometric amount or in an excess.

When carrying out processes (c), (d) and (e) according to the invention the reaction temperatures can be varied within a substantial range. In general, the process is carried out at temperatures between −20° C. and 150° C., preferably at temperatures between 0° C. and 80° C., For carrying out process (d) according to the invention, 0.8 to 2.5 mol, preferably 1.0 to 1.5 mol, of hydroxylamine or its ammonium compound $R^3ONH_2$ or $R^3ONH_3^{\oplus}W^{\ominus}$ and, if appropriate, 0.8 to 2.5 mol, preferably 1.0 to 1.5 mol, of reaction auxiliary are generally employed per mole of thieno[3,2-b]pyran-5,7-dione of the formula (I). $W^{\ominus}$ in this context represents an anion of an inorganic acid such as chloride, bromide, iodide, hydrogen sulphate or phosphate.

For carrying out process (e) according to the invention, 0.8 to 2.5 mol, preferably 1.0 to 1,5 mol, of organohalogen compound of the formula (IX) and, if appropriate, 0.8 to 2.5 mol, preferably 1.0 to 1,5 mol, of reaction auxiliary are generally employed per mole of thieno[3,2-b]pyran-5,7-dione of the formula (I) in which R¹ represents hydrogen.

The reaction is carried out and the reaction products are worked up and isolated by generally customary methods (cf. also the Preparation Examples).

While having a favourable toxicity to warm-blooded species, the active compounds are suitable for combating pathogenic endoparasites which occur in humans and in productive livestock, breeding animals, zoo animals, laboratory animals, experimental animals and pets in animal keeping and livestock breeding. They are active against all or individual stages of development of the pests and against resistant and normally sensitive strains. By combating the pathogenic endoparasites, it is intended to reduce disease, deaths and reduced performance (for example in the production of meat, milk, wool, hides, eggs, honey etc.), so that more economical and simpler animal keeping is made possible by employing the active compounds. The pathogenic endoparasites include cestodes, trematodes, nematodes and acantocephala, in particular:

From the order of the Pseudophyllidea, for example Diphyllobothrium spp., Spirometra spp., Schistocephalus spp., Ligula spp., Bothridium spp., Diplogonoporus spp..

From the order of the Cyclophyllidea, for example Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp..

From the subclass of the Monogenea, for example Gyrodactylus spp., Dactylogyrus spp., Polystoma spp..

From the subclass of the Digenea, for example Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp-, Cotylophoron spp., Gigantocotyle spp., Fischoederius spp. Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp..

From the order of the Enoplida, for example Trichuris spp., Capillaria spp., Trichomosoides spp., Trichinella spp..

From the order of the Rhabditida, for example Micronema spp., Strongyloides spp..

From the order of the Strongylida, for example Stronylus spp., Triodontophorus spp., Oesophagodontus spp., Trichonema spp., Gyalocephalus spp., Cylindropharynx spp.,. Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..

From the order of the Oxyurida, for example Oxyuris spp., Enterobius spp., Passalurus spp., Syphacia spp., Aspiculuris spp., Heterakis spp..

From the order of the Ascaridia, for example Ascaris spp., Toxascaris spp., Toxocara spp., Parascaris spp., Anisakis spp., Ascaridia spp..

From the order of the Spirurida, for example Gnathostoma spp., Physaloptera spp., Thelazia spp., Gongylonema spp., Habronema spp., Parabronema spp., Draschia spp., Dracunculus spp..

From the order of the Filariida, for example Stephanofilaria spp., Parafilaria spp., Setaria spp., Loa spp.,.Dirofilaria spp., Litomosoides spp., Brugia spp., Wuchereria spp., Onchocerca spp..

From the order of the Gigantorhynchida, for example Filicollis spp., Moniliformis spp., Macracanthorhynchus spp., Prosthenorchis spp..

The productive livestock and breeding animals include mammals such as, for example, cattle, horses, sheep, pigs, goats, camels, water buffaloes, donkeys, rabbits, fallow deer, reindeer, fur-bearing animals such as, for example, minks, chinchilla, raccoon, birds such as, for example, chickens, geese, turkeys, ducks, fresh water and salt water fish such as, for example, trout, carp, eels, reptiles, insects such as, for example, honeybee and silk worm.

Laboratory and experimental animals include mice, rats, guinea pigs, golden hamsters, dogs and cats.

Pets include dogs and cats.

The administration can be prophylactic or therapeutic.

The active compounds are administered, directly or in the form of suitable preparations, enterally, parenterally, dermally, nasally, by treating the environment, or with the aid of active-compound-containing shaped articles, such as, for example, strips, plates, bands, collars, ear tags, limb bands or marking devices.

The active compounds are administered enterally, for example orally, in the form of powders, tablets, capsules, pastes, drinks, granules, orally administrable solutions, suspensions and emulsions, boli, medicated feed or drinking water. Dermal administration is effected, for example, in the form of dipping, spraying or pouring-on and spotting-on. Parenteral administration is effected, for example, in the form of injection (intramuscular, subcutaneous, intravenous, intraperitoneal) or by implants.

The following are suitable preparations:

solutions, such as solutions for injection, or else solutions, concentrated for oral administration after dilution, solutions for use on the skin or in body cavitities, pour-on or spot-on formulations, gels;

emulsions and suspension for oral or dermal administration and for injection; semi-solid preparations;

formulations in which the active compound is incorporated in a cream base or in an oil-in-water or water-in-oil emulsion base;

solid preparations such as powders, premixes or concentrates, granules, pellets, tablets, boli, capsules; aerosols and inhalants, shaped articles containing active compounds.

Solutions for injection are administered intravenously, intramuscularly and subcutaneously.

Solutions for injections are prepared by dissolving the active compound in a suitable solvent and, if desired, adding additives such as solubilisers, acids, bases, buffer salts, antioxidants or preservatives. The solutions are sterile-filtered and decanted.

The following may be mentioned as solvents: physiologically acceptable solvents such as water, alcohols such as ethanol, butanol, benzyl acohol, glycerol, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilisers: solvents which aid the dissolution of the active compound in the main solvent, or which prevent its precipitation. Examples are polyvinylpyrrolidone, polyoxyethylated castor oil or polyoxyethylated sorbitan esters.

Preservatives are: benzyl alcohol, trichlorobutanol, p-hydroxybenzoic esters, n-butanol.

Oral solutions are administered directly. Concentrates are administered orally after previous dilution to the use concentrations. Oral solutions and concentrates are prepared as described above in the case of the solutions for injection and working under sterile conditions can be dispensed with.

Solutions for use on the skin are administered dropwise, painted on, rubbed in, sprinkled on or sprayed on. These solutions are prepared as described above in the case of the solutions for injection.

It may be advantageous to add thickeners during preparation. Thickeners are: inorganic thickeners such as bentonites, colloidal silica, aluminum monostearate, or organic thickeners such as cellulose derivatives, polyvinyl alcohols and their copolymers, acrylates and methacrylates.

Gels are applied to the skin or painted on the skin or incorporated into body cavities. Gels are prepared by adding such an amount of thickener to solutions which have been prepared as described in the case of the solutions for injection, that the result is a clear composition of cream-like consistency. The thickeners used are the thickeners mentioned further above.

Pour-on or spot-on formulations are poured or sprinkled onto limited area of the skin, the active compound penetrating the skin and acting systemically.

Pour-on or spot-on formulations are prepared by dissolving, suspending or emulsifying the active compound in suitable dermatologically acceptable solvents or solvent mixtures. If desired, further adjuvants such as colorants, resorption accelerators, antioxidants, agents which impart protection against light, or tackifiers, are added.

The following may be mentioned as solvents: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol monobutyl ether, ketones such as acetone, methyl ethyl ketone, aromatic and/or aliphatic hydrocarbons, vegetable or synthetic oils, DMF, dimethylacetamide, N-methylpyrrolidone, 2,2-dimethyl-4-oxy-methylene-1,3-dioxolane.

Colorants are all colorants which are released for use on animals and which can be suspended or dissolved.

Resorption accelerators are, for example, DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Agents which impart protection against light are, for example, novantisolic acid.

Tackifiers are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenising this phase with the solvent of the other phase, with the aid of suitable emulsifiers and, if appropriate, further adjuvants such as colorants, resorption accelerators, preservatives, antioxidants, agents which impart protection against light, viscosity-increasing substances.

The following may be mentioned as hydrophobic phase (oil): paraffin oils, silicone oils, natural vegetable oils such as sesame seed oil, almond oil, castor oil, synthetic triglycerides such as caprilic/caproic acid bigylceride, triglyceride mixture with vegetable fatty acids of chain length $C_{8-12}$ or other specifically selected natural fatty acids, partial glyceride mixtures of saturated or unsaturated, optionally also hydroxylcontaining, fatty acids, mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/caproic acid esters of saturated fatty alcohols of chain length $C_{12}$–$C_{18}$, isopropyl stearate, oleyl oleate, decyl oleate, ethyl oleate, ethyl lactate, waxy fatty acid esters such as artificial duck's uropygial fat, dibutyl phthalate, diisopropyl adipate, ester mixtures related to the latter, etc.

Fatty alcohols such as isotridecyl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: nonionic surfactants, for example polyoxyethylated castor oil, polyoxyethylated sorbitan monooleate, sorbitan monostearate, glycerol monostearate, polyoxyethyl stearate, alkylphenol polyglycol ethers; ampholytic surfactants such as disodium N-lauryl-β-iminodipropionate or lecithin; anionic surfactants such as Na lauryl sulphate, fatty alcohol ether sulphates, the monoethanolamine salt of mono/dialkyl polyglycol ether orthophosphoric esters; cationic surfactants such as cetyltrimethylammonium chloride.

The following may be mentioned as further adjuvants: caprylic/caproic acid esters of saturated fatty alcohols of chain length $C_{12}$–$C_{18}$, isopropyl stearate, oleyl oleate, decyl oleate, ethyl oleate, ethyl lactate, waxy fatty acid esters such as artificial duck's uropygial fat, dibutyl phthalate, diisopropyl adipate, ester mixtures related to the latter, etc.

Fatty alcohols such as isotridec-yl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: nonionic surfactants, for example polyoxyethylated castor oil, polyoxyethylated sorbitan monooleate, sorbitan monostearate, glycerol monostearate, polyoxyethyl stearate, alkylphenol polyglycol ethers; ampholytic surfactants such as disodium N-lauryl-$\beta$-iminodipropionate or lecithin; anionic surfactants such as Na lauryl sulphate, fatty alcohol ether sulphates, the monoethanolamine salt of mono/dialkyl polyglycol ether orthophosphoric esters; cationic surfactants such as cetyltrimethylammonium chloride.

The following may be mentioned as further adjuvants: viscosity-increasing and emulsion-stabilising substances such as carboxymethylcellulose, methylcellulose and other cellulose derivatives and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica, or mixtures of the substances listed.

Suspensions can be administered orally, dermally or as injections. They are prepared by suspending the active compound in an excipient liquid, if appropriate with the addition of further adjuvants such as wetting agents, colorants, resorption accelerators, preservatives, antioxidants agents which impart protection against light.

Excipient liquids which may be mentioned are all homogenous solvents and solvent mixtures.

Wetting agents (dispersants) which may be mentioned are the surfactants given further above.

Other adjuvants which may be mentioned are those given further above.

Semi-solid preparations can be administered orally or dermally. They differ from the above-described suspensions and emulsions only on the basis of their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Inorganic substances are, for example, sodium chloride, carbonates such as calcium carbonate, hydrogen carbonates, aluminum oxides, silicas, clays, precipitated or colloidal silicon dioxide, phosphates.

Organic substances are, for example, sugars, cellulose, foodstuffs and animal feeds such as powdered milk, animal meals, cereal meals and coarse cereal meals, and starches.

Adjuvants are preservatives, antioxidants, colorants, which have already been mentioned further above.

Other suitable adjuvants are lubricants and gliding agents such as, for example, magnesium stearate, stearic acid, talc, bentonites, substances which promote disintegration such as starch or crosslinked polyvinylpyrrolidone, binders such as, for example, starch, gelatin or linear polyvinylpyrrolidone, and also dry binders such as microcrystalline cellulose.

The active compounds can exist in the preparations also as a mixture with synergists or with other active compounds which act against pathogenic endoparasites. Such active compounds are, for example, L-2,3,5,6-tetrahydro-6-phenylimidazothiazole, benzimidazole carbamates, praziquantel, pyrantel, febantel.

Ready-for-use preparations contain the active compound in concentrations from 10 ppm-20 per cent by weight, preferably from 0.1-10 per cent by weight.

Preparations which are diluted prior to use contain the active compound in concentrations from 0.5-90 per cent by weight, preferably from 5 to 50 per cent by weight.

In general, it has proved advantageous to administer amounts of approximately 1 to approximately 100 mg of active compound per kg of body weight per day to achieve effective results.

The active compounds according to the invention can be used as defoliants, desiccants, agents for destroying broad-leaved plants and, especially, as weed-killers and growth regulators. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants: Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

The compounds of the formula (I) according to the invention are suitable for selectively combating monocotyledon weeds in monocotyledon and dicotyledon cultures, both by the pre-emergence and the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are prepared in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground syn minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides such as, for example, N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet, and 4-amino-6-(1,1-dimethylethyl)-3-methylthio-1,2,4-triazin-5(4H)-one (METRIBUZIN) for combating weeds in soya beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); methyl2-[[[[[(4,6-dimethoxypyrimidin-2-yl)-amino]-carbonyl]-amino]-sulphonyl]-methyl]-benzoate (BENSULFURON); 3-isopropyl-2,1,3-benzothiadiazin-4-one 2,2-dioxide (BENTAZONE); 3,5-dibromo-4-hydroxy-benzonitrile (BROMOXYNIL); 5-amino-4-chloro-2-phenyl-2,3-dihydro-3-oxy-pyridazrne (CHLORIDAZON); 2-chloro-N-{[(4-methoxy-6-methyl-1,3,5-triazin-2-yl)-amino]-carbonyl}-benzene-sulphonamide (CHLORSULFURON); N,N-dimethyl-N'-(3-chloro-4-methylphenyl)-urea (CHLOR/TOLURON); 5-(2-chloro-4-(trifluoromethyl)phenoxy)-2-nitrobenzoic acid (ACIFLUORFEN); methyl 5-(2,4-dichloro-phenoxy}-2-nitrobenzoate (BIFENOX); 5-(2-chloro-4-(trifluoromethyl)-phenoxy)-N-methylsulphonyl-2-nitrobenzamide (FOMESAFEN); 2-ethoxy-1-methyl-2-oxo-ethyl 5-(2-chloro-4-trifluoro-methyl)-phenoxy)-2-nitrobenzoate (LACTOFEN); 2-[4,5-dihydro-4-methyl-4-(1-methylethyl-5-oxo-1H-imidazol-2-yl]-5-ethyl-3-pyridine carboxylic acid (IMAZETHAPYR); 2-(4,5-dihydro-4-methyl-4-(1-methylethyl)-5-oxo-1H-imidazol-2-yl)-3-quinoline-carboxylic acid (IMAZAQUIN);ethyl2-((4-chloro-6-methoxy-2-pyrimidinyl)-aminocarbonyl)-aminosulphonyl)-benzoate (CHLORIMURON); 4-amino-6-t-butyl-3-ethylthio-1,2,4-triazin-5(4H)-one (ETHIOZIN); N-(3-trifluoromethylphenyl)-N,N-dimethylurea (FLUOMETURON); [(4-amino-3,5-dichloro-6-fluoro-2-pyridinyl)-oxy]-acetic acid or its 1-methylheptyl ester (FLUROXYPYR);methyl2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl--4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-{[[(((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline (PENDIMETHALIN); 3-(ethoxycarbonylaminophenyl) N-(3,-methylphenyl)-carbamate (PHENMEDIPHAM); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); 2,6-dinitro-4-trifluoromethyl-N,N'-dipropylaniline (TRIFLURALIN). Surprisingly, some mixtures also show a synergistic action.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect In general, the amounts used are between 10 g and 10 kg of active compound per hectare of soil surface, preferably between 5 g and 5 kg per ha.

The preparation and use of the active compounds according to the invention can be seen from the following examples.

SYNTHESIS EXAMPLES

Example 1

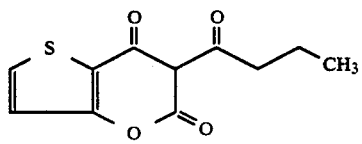

Thieno[3,2-b]-6-butyryl-pyran-5,7-dione
by process (b)

18.64 g (0.111 mol) of thieno[3,2-b]pyran-5,7-dione are initially introduced together with 80 ml of butyric acid. 30 ml of phosphoryl chloride are then added dropwise, and the mixture is stirred for 2 hours at 80° C. It is allowed to cool and 60 ml of ethanol are carefully added dropwise with cooling. The precipitate which has separated out is filtered off with suction and washed with a little ethanol.

For purification, the product is recrystallised from ethanol.

Yield: 10.80 g (40.85% of theory)
Melting point: 108°–109° C.

EXAMPLE 2

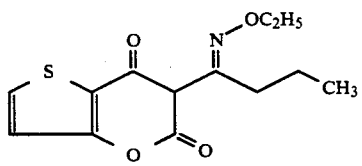

by process (d)
Thieno[3,2-b]-6-(1-ethoxyiminobutyl)-pyran-5,7-dione 4.76 g (0.02 mol) of Thieno[3,2-b]-6-butyryl-pyran-5,7-dione are initially introduced together with 60 ml of methanol. 2.00 g (0.024 mol) of sodium hydrogencarbonate and 2.34 g (0.24 mol) of ethoxyamine hydrochloride are then added. The mixture is stirred at room temperature and subsequently concentrated to dryness. The residue is taken up in 50 ml of methylene chloride, the mixture is washed once with water, twice with saturated sodium hydrogen-carbonate solution and again with water, dried with sodium sulphate, and the solvent is removed in vacuo. 2.8 g (49.8% of theory) of oxime ether of melting point m.p. 61°–62° C. are obtained.

EXAMPLE 2a

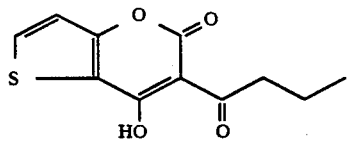

Thieno[3.2-b]-6-butyryl-pyran-5,7-dione
by process (a)

Step 1

33.64 g (0.02 mol) of thieno-[3,2-b]pyran-5,7-dione are initially introduced together with 50 ml of methylene chloride and 26.24 g (0.26 mol) of triethylamine, a solution of 23.60 g (0.22 mol) of butyryl chloride in 40 ml of methylene chloride is added dropwise, and the mixture is refluxed for 4 hours and stirred for 12 hours at 20° C. The solution is poured into 200 ml of water, and the organic phase is dried with magnesium sulphate and the solvent removed in vacuo. The crude product is purified by chromatography (silica gel, methylene chloride), and the solvent is removed in vacuo. 26.5 g (56% of theory) of thieno [3,2-b]-7-butyryloxy-pyran-5-one of melting point m.p.: 55°–56° C. are obtained.

Step 2

8.90 g (0.037 mol) of thieno[3,2-b]7-butyryloxy-pyran-5-one are initially introduced together with 50 ml of 1,2-dichloroethane. 9.87 g (0.074 mol) of aluminium chloride are then added. The mixture is stirred for 2 hours at 20° C. and then evaporated in vacuo on a rotary evaporator. The residue is then poured onto 60 g of ice and 60 ml of concentrated hydrochloric acid and the mixture is subjected to filtration with suction. The precipitate is subsequently stirred into 300 ml of 7N NaOH and again subjected to filtration with suction. The mother liquor is then acidified and the precipitate is filtered off with suction. 1.20 g (13.5% of theory) of thieno[3,2-b]-6-butyryl-pyran-5,7-dione of melting point m.p.: 108°14 109° C. are obtained.

Example 2b

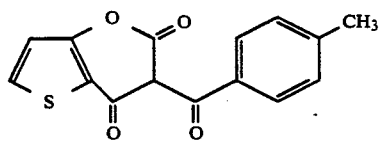

by process (c)
Thieno[3,2-b]-6-(4-methyl)-benzoyl-pyran-5,7-dione 15.46 (0.10 mol) of 3-methylbenzoyl chloride and 2.73 g (0.02 mol) of zinc chloride are initially introduced together with 100 ml of toluene, and then 16.82 g (0.10 mol) of thieno[3,2-b]pyran-5,7-dione is added slowly at 20° C. After stirring at 20° C. for 12 hours the solvent is removed in vacuo and the residue is stirred with ether. Following filtration with suction the crude product is recrystallised from acetonitrile. Yield: 13.63 g (48% of theory) Melting point: 167°–168° C.

Example 2c

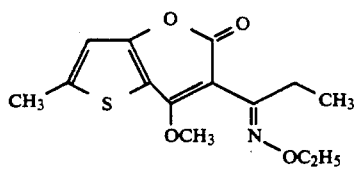

Thieno[3,2-b]-6-(1-ethoxyiminopropyl)-7-methoxy-pyran-5-one by process (e)

0.50 g (1.78 mmol) of thieno[3,2-b]-6-(1-ethoxyiminopropyl)-pyran-5,7-dione are initially introduced together with 30 ml of acetone. 0.33 g (2.31 mmol) of iodomethane and 0.25 g (1.78 mmol) of potassium, carbonate are then added. The mixture is heated under reflux for 14 hours, allowed to cool and then evaporated to dryness. The residue is taken up into 100 ml of dichloromethane, washed twice with water, dried over magnesium sulphate and the solvent removed in vacuo to give an oily product.

Yield: 0.43 g (82% of theory)

$^7$NMR(DMSO)$\delta$ = 1.05–1.35 (6H, t, 2×CH$_3$), 2.50 (3H, s, CH$_3$), 2.70 (2H, q, CH$_2$), 4.10 (3H, s, OCH$_3$), 4.20 (2H, q, OCH$_2$), 6.75 (7H, d, thiophene-H) ppm.

TABLE 1

Preparation Examples of the compound of the formula (I)

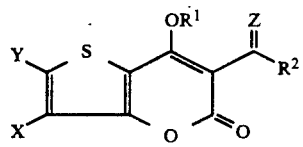

| No. | X | Y | Z | R$^1$ | R$^2$ | m.p. [°C] |
|---|---|---|---|---|---|---|
| 3 | H | H | N—O—CH$_3$ | H | Propyl | 87–88 |
| 4 | H | H | N—O—CH$_2$—CH=CH$_2$ | H | Propyl | |
| 5 | H | H | N—O—CH$_2$—CH=CHCl | H | Propyl | |
| 6 | CH$_3$ | H | N—O—C$_2$H$_5$ | H | Propyl | 104–105 |
| 7 | CH$_3$ | H | N—O—CH$_2$—CH=CH$_2$ | H | Propyl | |
| 8 | CH$_3$ | H | N—O—CH$_2$—CH=CHCl | H | Propyl | |
| 9 | H | CH$_3$ | O | H | Propyl | 138 |
| 10 | H | CH$_3$ | N—OC$_2$H$_5$ | H | Propyl | 86–87 |
| 11 | H | CH$_3$ | N—OCH$_3$ | H | Propyl | 87–88 |
| 12 | H | CH$_3$ | N—O—CH$_2$—CH=CH$_2$ | H | Propyl | |
| 13 | H | CH$_3$ | N—O—CH$_2$—CH=CHCl | H | Propyl | |
| 14 | CH$_3$ | CH$_3$ | N—OC$_2$H$_5$ | H | Propyl | |
| 15 | CH$_3$ | CH$_3$ | N—O—CH$_2$—CH=CH$_2$ | H | Propyl | |
| 16 | CH$_3$ | CH$_3$ | N—O—CH$_2$—CH=CHCl | H | Propyl | |
| 17 | C$_2$H$_5$ | H | N—OC$_2$H$_5$ | H | Propyl | |
| 18 | H | C$_2$H$_5$ | N—OC$_2$H$_5$ | H | Propyl | |
| 19 | H | Cl | N—OC$_2$H$_5$ | H | Propyl | |
| 20 | Cl | H | N—OC$_2$H$_5$ | H | Propyl | |
| 21 | Cl | Cl | N—OC$_2$H$_5$ | H | Propyl | |
| 22 | H | H | O | H | Ethyl | |
| 23 | H | H | N—O—CH$_2$—CH=CH$_2$ | H | Ethyl | |
| 24 | H | H | N—O—CH$_2$—CH=CHCl | H | Ethyl | |
| 25 | H | CH$_3$ | O | H | Ethyl | 163–164 |
| 26 | H | CH$_3$ | N—OC$_2$H$_5$ | H | Ethyl | 131–132 |
| 27 | H | CH$_3$ | N—O—CH$_2$—CH=CH$_2$ | H | Ethyl | 81–82 |

TABLE 1-continued

Preparation Examples of the compound of the formula (I)

$$\text{(I)}$$

(Structure: thiophene fused pyranone with substituents Y, X on thiophene, OR$^1$, and =Z-CHR$^2$ / C=O)

| No. | X | Y | Z | R$^1$ | R$^2$ | m.p. [°C.] |
|---|---|---|---|---|---|---|
| 28 | H | CH$_3$ | N—O—CH$_2$—CH=CHCl | H | Ethyl | |
| 29 | CH$_3$ | H | N—O—CH$_2$—CH=CH$_2$ | H | Ethyl | |
| 30 | CH$_3$ | H | N—O—CH$_2$—CH=CHCl | H | Ethyl | |
| 31 | Cl | Cl | N—O—CH$_2$—CH=CH$_2$ | H | Ethyl | |
| 32 | Cl | H | N—O—CH$_2$—CH=CHCl | H | Ethyl | |
| 33 | H | Cl | N—O—CH$_2$—CH=CHCl | H | Ethyl | |
| 34 | Br | H | N—O—CH$_2$—CH=CH$_2$ | H | Ethyl | |
| 35 | H | SCH$_3$ | N—O—CH$_2$—CH=CHCl | H | Ethyl | |
| 36 | H | OCH$_3$ | N—O—CH$_2$—CH=CHCl | H | Ethyl | |
| 37 | CH$_3$ | H | O | H | Propyl | 75–76 |
| 38 | CH$_3$ | H | O | H | Ethyl | 89–90 |
| 39 | H | H | O | H | Methyl | |
| 40 | H | H | O | H | Propyl | |
| 41 | H | H | O | H | 4-Cl-C$_6$H$_4$— | |
| 42 | H | H | O | H | 4-OCF$_3$-C$_6$H$_4$— | |
| 43 | H | H | O | H | 4-SCF$_3$-C$_6$H$_4$— | |
| 44 | H | H | O | H | 4-Me-C$_6$H$_4$— | |
| 45 | H | H | O | H | 3,4-Cl$_2$-C$_6$H$_3$— | |
| 46 | H | H | O | H | 3-Cl-4-CF$_3$-C$_6$H$_3$— | |

TABLE 1-continued

Preparation Examples of the compound of the formula (I)

| No. | X | Y | Z | R¹ | R² | m.p. [°C.] |
|-----|---|---|---|----|----|-----------|
| 47 | H | H | N—OCH₂—(4-Cl-phenyl) | H | Methyl | |
| 48 | H | H | N—OCH₂—(4-OCF₃-phenyl) | H | Methyl | |
| 49 | H | H | N—OCH₂—(4-SCF₃-phenyl) | H | Methyl | |
| 50 | H | H | N—OCH₂—(4-Me-phenyl) | H | Methyl | |
| 51 | H | H | N—OCH₂—(3,4-diCl-phenyl) | H | Methyl | |
| 52 | H | H | N—OCH₂—(2-Cl-4-CF₃-phenyl) | H | Methyl | |
| 53 | H | H | N—OCH₂—(4-Cl-phenyl) | H | Ethyl | |
| 54 | H | H | N—OCH₂—(4-OCF₃-phenyl) | H | Ethyl | |
| 55 | H | H | N—OCH₂—(4-SCF₃-phenyl) | H | Ethyl | |
| 56 | H | H | N—OCH₂—(4-Me-phenyl) | H | Ethyl | |
| 57 | H | H | N—OCH₂—(3,4-diCl-phenyl) | H | Ethyl | |

TABLE 1-continued

Preparation Examples of the compound of the formula (I)

$$\text{(I)}$$

| No. | X | Y | Z | R$^1$ | R$^2$ | m.p. [°C.] |
|---|---|---|---|---|---|---|
| 58 | H | H | N—OCH$_2$—(2-Cl, 4-CF$_3$-phenyl) | H | Ethyl | |
| 59 | H | H | N—OCH$_2$—(4-Cl-phenyl) | H | Propyl | |
| 60 | H | H | N—OCH$_2$—(4-OCF$_3$-phenyl) | H | Propyl | |
| 61 | H | H | N—OCH$_2$—(4-SCF$_3$-phenyl) | H | Propyl | |
| 62 | H | H | N—OCH$_2$—(4-Me-phenyl) | H | Propyl | |
| 63 | H | H | N—OCH$_2$—(3,4-Cl$_2$-phenyl) | H | Propyl | |
| 64 | H | H | N—OCH$_2$—(2-Cl, 4-CF$_3$-phenyl) | H | Propyl | |
| 65 | H | H | N—O—CH$_3$ | H | 4-Cl-phenyl | |
| 66 | H | H | N—O—C$_2$H$_5$ | H | 4-Cl-phenyl | |
| 67 | H | H | N—O—CH$_3$ | H | 4-OCF$_3$-phenyl | |
| 68 | H | H | N—O—C$_2$H$_5$ | H | 4-OCF$_3$-phenyl | |

TABLE 1-continued
Preparation Examples of the compound of the formula (I)
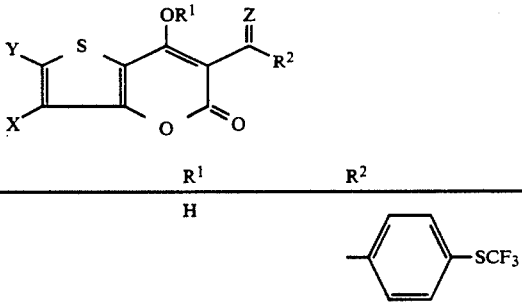
| No. | X | Y | Z | R¹ | R² | m.p. [°C.] |
|---|---|---|---|---|---|---|
| 69 | H | H | N—O—CH$_3$ | H | 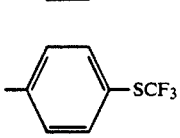 4-SCF$_3$-C$_6$H$_4$ | |
| 70 | H | H | N—O—C$_2$H$_5$ | H | 4-SCF$_3$-C$_6$H$_4$ | |
| 71 | H | H | N—O—CH$_3$ | H | 4-Me-C$_6$H$_4$ | |
| 72 | H | H | N—O—C$_2$H$_5$ | H | 4-Me-C$_6$H$_4$ | |
| 73 | H | H | N—O—CH$_3$ | H | 3,4-Cl$_2$-C$_6$H$_3$ | |
| 74 | H | H | N—O—C$_2$H$_5$ | H | 3,4-Cl$_2$-C$_6$H$_3$ | |
| 75 | H | H | N—O—CH$_3$ | H | 3-Cl-4-CF$_3$-C$_6$H$_3$ | |
| 76 | H | H | N—O—C$_2$H$_5$ | H | 3-Cl-4-CF$_3$-C$_6$H$_3$ | |
| 77 | H | H | O | C(=O)—CH$_2$CH$_2$CH$_3$ | Propyl | |

EXAMPLES OF THE PREPARATION OF THE EDUCTS

Synthesis of thieno-[3,2-b]pyran-5,7-dione

Example II-1

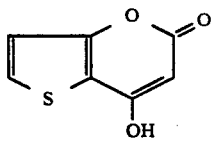

2.07 g (0.00966 mol) of 2-ethoxycarbonylacetyl-3-hydroxythiophene are refluxed for 1 hour together with 50 ml of absolute xylene. Meanwhile, the xylene is slowly distilled off, during which process the product separates out as a solid and is subsequently filtered off with suction.

Yield: 0.4 g (22% of theory)
Melting point: 223°14 225° C.
The following are synthesised analogously:

Examples II-2

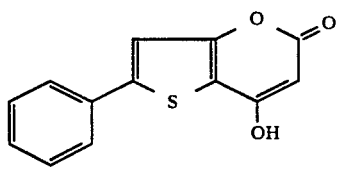

$C_{13}H_8O_3S$ Melting point: 214°-215° C.
NMR (CDCl$_3$): δ=5.6 (s, 1H), 7.2 (s, 1H), 7.4-7.6 (m, 5H) ppm
IR (KBr): 1640; 1560; 1480; 1400 cm$^{-1}$

Example II-3

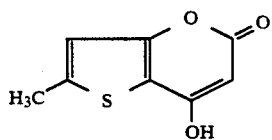

$C_8H_6O_3S$ Melting point: 210°-212° C.
IR (KBr): 1680; 1560; 1510; 1330 cm$^{-1}$
MS: 182 (65%); 140 (100%) 112 (30%)

Example II-4

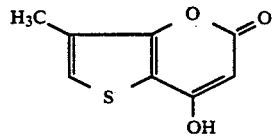

$C_8H_6O_3S$ Melting point: 220°-221° C.
NMR (DMSO): δ=2.25 (s, 3H); 5.4 (s, 2H); 7.6 (s, 1H) ppm

Synthesis of 2-ethoxycarbonylacetyl-3-hydroxy-thiophene

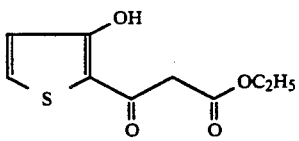

4.8 g (0.0337 mol) of 2-acetyl-3-hydroxythiophene in 150 ml of diethyl carbonate are heated to 90°-100° C. 5 g of small sodium pieces are then added. Stirring is continued for 15 hours at 90°-100° C. To decompose remainders of sodium, a little ethanol is added. For working up, the mixture is extracted twice using 75 ml of water, the aqueous phase is then acidified with 10 ml of concentrated HCl, extracted 3 times with 50 ml portions of ether, dried, distilled in vacuo, and the fraction between 70° and 100° C. (0.6 mbar, educt) and between 113° and 118° C. (0.4 mbar product) is collected.

The purification is carried out by means of column chromatography, using ethyl acetate/cyclohexane (1:1) as the eluant.

Yield: 0.5 g (6.9% of theory).

Synthesis of 2-acetyl-3-hydroxythiophene

Example V-1

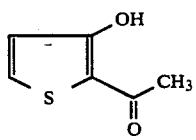

4.65 g (0.086 mol) of sodium methylate are suspended in 100 ml of toluene. A suspension of 7.6 g (0.0843 mol) of acetonylmercaptan in 150 ml of toluene is then added. After this, 7.1 g (0.0843 mol) of methyl propiolate are added dropwise. The mixture is refluxed for 1 hour. After cooling, a solution of 4.5 ml of concentrated H$_2$SO$_4$ in 120 ml of water is added dropwise. The toluene phase is separated off and washed 3 times using 50 ml portions of water, dried and concentrated. The batch is distilled and the crude fraction is collected between 85° C. and 90° C. at 15.9 mbar. Weight of the crude product: 6 g. The crude product is introduced into 48 ml of 1N NaOH, and the mixture is extracted using ether. The aqueous phase is acidified using 2N HCl and extracted with ether. After the mixture has been dried and concentrated in vacuo, it is triturated with ether.

Yield: 1.2 g (10% of theory)
Melting point: 48°-50° C.
The following were synthesised analogously:

Example V-2

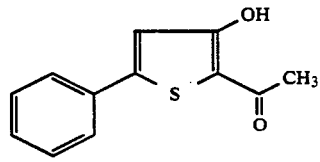

$C_{12}H_{10}O_2S$ Melting point: 93°-94° C.
NMR (CDCl$_3$): δ=2.4 (s,3H), 7.0 (s, 1H), 7.4 (m,3H), 7.6 (m, 2H), 11.6 (s, 1H) ppm IR (KBr): 1600; 1480; 1420; 1370; 1340 cm$^{-1}$

Example V-3

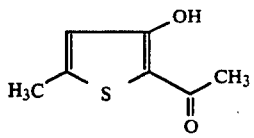

C$_7$H$_8$O$_2$S (Process α)

42.1 g (0.78 mol) of sodium methylate are suspended in 1000 ml of toluene. 70.3 g (0.78 mol) of 2,5-dihydroxy-2,5-dimethyl-1,4-dithiane and 190 g (1.28 mol) of ethyl β-chloro-crotonate are added.

The mixture is subsequently refluxed for 2 hours. It is allowed to cool, and a solution of 41.7 ml of concentrated H$_2$SO$_4$ in 1100 ml of water is added to the reaction mixture.

The organic phase is separated off, and the aqueous phase is re-extracted with toluene. The combined organic phases are washed with water and subsequently dried over sodium sulphate.

After the desiccant has been filtered off, the solvent is removed in vacuo. The residue is introduced into 450 ml of 1N NaOH solution and extracted once with ether. The aqueous phase is acidified with 2N HCl and extracted with ether. The organic phases are dried over sodium sulphate. After the desiccant has been separated off and the solvent has been removed in vacuo, the residue is crystallised by trituration with ether.

Yield: 20 g (16% of theory)
Melting point: 74°–75° C.
IR (KBr): 1490; 1440; 1220; 1040 cm$^{-1}$
NMR (CDCl$_3$) δ=2.3 (s, 3H); 2.45 (d, 3H); 6.5 (d, 1H); 11.7 (s, 1H) ppm
MS: 156 (100%); 141 (100%)

Process β)

A solution of 2.92 g (0.02 mol) of ethyl β-thioacetoacetate in 10 ml of absolute benzene is added dropwise to a solution of 0.6 g (0.025 mol) of sodium hydride in 50 ml of absolute benzene, under a nitrogen atmosphere.

The mixture is subsequently refluxed for 30 minutes. 2.78 g (0.03 mol) of chloroacetone, dissolved in 20 ml of absolute benzene, are then added dropwise, and the mixture is refluxed for another 3 hours. After this, the batch is poured into ice-water and acidified. The organic phase is separated off, and the solvent is removed in vacuo.

The residue is taken up in 100 ml of absolute DMSO. Under a nitrogen atmosphere, 0.72 g (0.03 mol) of sodium hydride are added and the batch is subsequently stirred for 2 hours. The batch is subsequently introduced into water and acidified. The aqueous phase is extracted with ether and the organic phase is dried over sodium sulphate.

After removing the solvent in vacuo, the product is purified by chromatography (eluent: ethyl acetate/cyclohexane 1:1).

Yield: 470 mg (15% of theory)
The following were synthesised analogously:

Example V-4

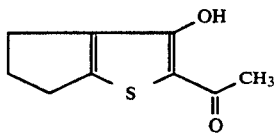

C$_9$H$_{10}$O$_2$S (pale yellow oil)
NMR (CDCl$_3$): δ=2.3 (s, 3H); 2.4–2.5 (m, 2H); 2.6–2.7 (m, 2H); 2.85–2.95 (m, 2H); 11.8 (s, 1H) ppm
MS: 182 (56%); 167 (100%)

Example V-5

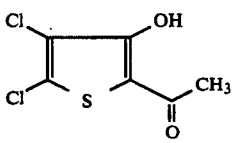

C$_6$H$_4$Cl$_2$O$_2$S Melting point: 84°–85° C.
NMR (CDCl$_3$): δ=2.15 (s, 3H); 11.9 (s, 1H) ppm

Example V-6

Synthesis of 2-acetyl-3-hydroxy-4-methylthiophene

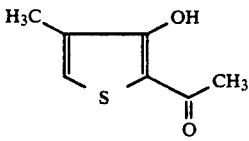

36.0 g (0.227 mol) of 2-acetyl-3-keto-4-methyl-4,5-dihydrothiophene are initially introduced into 260 ml of methylene chloride 21.9 ml of sulphuryl chloride in 260 ml of methylene chloride are then added dropwise at 0° C. While the sulphuryl chloride/methylene chloride mixture is added dropwise, a stream of nitrogen is passed into the solution to expel the HCl gas which is formed. When the addition is complete, stirring is continued for 30 minutes at 10°–15° C. The mixture is then introduced into 600 ml of water, and the organic phase is extracted with a 5% strength NaHCO$_3$ solution, dried and concentrated in vacuo.

For purification, the product is distilled.
Yield: 23.1 g (65% of theory)
Boiling point: 112°–115° C. (1.0 mbar)
Melting point: 42°–43° C.

Synthesis of 2-acetyl-3-keto-4-methyl-4,5-dihydrothiophene

[(VI), R'=CH$_3$; R=H]

Example VI-1

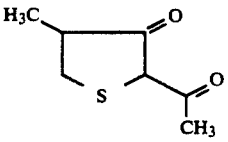

26.13 g (~0.5 mol) of sodium methylate are suspended in 1.0 l of toluene. 88.15 g (0.5 mol) of methyl 3-acetonylmercaptopropionate are then added dropwise at 70° C., and stirring is continued for 3 hours at 70° C. The mixture is allowed to cool and introduced into a mixture of 750 ml of ice-water and 60 ml of glacial acetic acid. The organic phase is separated off and stirred into 1.5 l of 10% strength sodium hydroxide solution. The aqueous phase is acidified using glacial acetic acid and extracted with methylene chloride, dried, and concentrated in vacuo.

For purification, the product is distilled.
Yield: 38.6 g (53.4% of theory)
Boiling point: 63°–65° C. (0.5 mbar)

Synthesis of methyl 3-acetonylmercaptopropionate

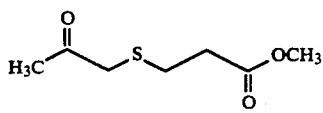

90.1 g (0.5 mol) of 2,5-dihydroxy-2,5-dimethyl-1,4-dithiane are initially introduced into 100 ml of absolute tetrahydrofuran. 1.0 g of piperidine is then added, and 94.7 g (0.945 mol) of methyl acrylate are added dropwise at 10°–15° C, during which process another two portions of 0.5 g of piperidine are added at the same time. The mixture is subsequently stirred for 60 minutes at 60° C. It is allowed to cool and introduced into 500 ml of water.

The mixture is extracted with methylene chloride, dried, and concentrated in vacuo. For purification, the product is distilled.
Yield: 147.30 g (81.9% of theory)
Boiling point: 98°–100° C. (2.1 mbar)

Example A

In-vivo nematode test

Trichostrongylus colubriformis/sheep

Sheep which had been infected experimentally with Trichostrongylus colubriformis were treated after the prepatency time of the parasite had elapsed. The active compounds were administered orally in the form of pure active compound in gelatin capsules.

The degree of effectiveness is determined by counting the worm eggs excreted with the faeces before and after the treatment.

Complete standstill of egg excretion after the treatment means that the worms were expelled or damaged in such a way that they no longer produce eggs (dosis effectiva).

Tested active compounds and effective dosage rates (dosis effectiva) can be seen from the table which follows.

| Active compound Example No. | dosis effectiva in mg/kg |
|---|---|
| 26 | 100 |

Example B

In-vivo nematode test

Haemonchus contortus/sheep

Sheep which had been infected experimentally with Haemonchus contortus were treated after the prepatency time of the parasite had elapsed. The active compounds were administered orally in the form of pure active compound in gelatin capsules.

The degree of effectiveness is determined by counting the worm eggs excreted with the faeces before and after the treatment.

Complete standstill of egg excretion after the treatment means that the worms were expelled or damaged in such a way that they no longer produce eggs (dosis effectiva).

Tested active compounds and effective dosage rates (dosis effectiva) can be seen from the table which follows.

| Active compound Example No. | dosis effectiva in mg/kg |
|---|---|
| 26 | 50 |

Example C

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a powerful action against weeds is shown by the compounds of Preparation Examples 10, 26 and 27, while displaying a good compatibility with crop plants such as, for example, oilseed rape and soya bean.

Example D

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control.

The figures denote:
0% = no action (like untreated control)
100% = total destruction A clearly superior activity against weeds compared with the prior art is shown in this test, for example, by the compounds according to Preparation Examples 10, 26 and 27, while displaying good compatibility with crop plants such as, for example, wheat, sugar beet and oilseed rape.

We claim:

1. A substituted thieno[3,2-b]pyran-5,7-dione of the formula

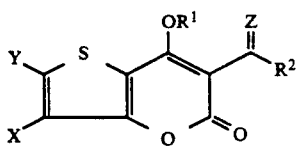

or a tautomer thereof,
in which
$R^1$ represents hydrogen, or a straight-chain or branched radical selected from the group consisting of alkyl, alkenyl, alkynyl, alkylsulphonyl, alkylcarbonyl, alkenylcarbonyl, and in each case optionally substituted phenyl, benzoyl or benzenesulphonyl, $R^2$ represents a straight-chain or branched radical selected from the group consisting of alkyl, alkenyl, alkynyl, halogenoalkyl, cycloalkyl, and in each case optionally substituted phenyl or benzyl, X and Y independently of one another represent hydrogen, halogen, cyano, nitro, straight-chain or branched alkyl, alkenyl, alkynyl, halogenoalkyl, cycloalkyl, alkylcarbonyl, alkoxycarbonyl, alkyloxy, alkylthio, halogenoalkoxy, halogenoalkylthio, alkylamino, dialkylamino, or in each case optionally substituted aryl, aralkyl, aryloxy or arylthio, or X and Y together with the adjoining C atoms form a carbocyclic ring which consists of 4 to 8 carbon atoms and which is optionally interrupted by at least one of nitrogen, oxygen and sulphur, and represents oxygen or $NOR^3$,
where
$R^3$ represents hydrogen, or a straight-chain or branched radical selected from the group consisting of alkyl, alkenyl, alkynyl, halogenoalkyl, halogenoalkyenyl, halogenoalkinyl, cycloalkyl, and optionally substituted phenyl or phenylalkyl, or a salt thereof.

2. A substituted thieno[3,2-b]pyran-5,7-dione or tautomer or salt thereof according to claim 1, in which
$R^1$ represents hydrogen, or a straight-chain or branched radical selected from the group consisting of $C_1$–$C_7$-alkyl, $C_3$–$C_6$-alkenyl, $C_3$–$C_6$-alkynyl, $C_1$–$C_6$-alkylsulphonyl, $C_1$–$C_6$-alkylcarbonyl, $C_1$–$C_6$-alkenylcarbonyl, and in each case optionally substituted phenyl, benzenesulphonyl, or benzoyl, $R^2$ represents a straight-chain or branched radical selected from the group consisting of $C_1$–$C_7$-alkyl, $C_2$–$C_6$-alkenyl, $C_3$–$C_6$-alkynyl, $C_1$–$C_7$-halogenoalkyl having 1 to 15 identical or different halogen atoms, $C_3$–$C_7$-cycloalkyl, and in each case optionally substituted phenyl, or benzyl, X and Y independently of one another represent hydrogen, halogen, cyano, nitro, straight-chain or branched $C_1$–$C_7$-alkyl, $C_2$–$C_6$-alkenyl, $C_2$–$C_6$-alkynyl, $C_1$–$C_7$-halogenoalkyl having 1 to 15 identical or different halogen atoms, $C_3$–$C_6$-cycloalkyl, $C_1$–$C_7$-alkylcarbonyl, $C_1$–$C_7$-alkyloxycarbonyl, $C_1$–$C_7$-alkyloxy, $C_1$–$C_7$-alkylthio, 1–5 halogeno-$C_{1-4}$-alkyloxy, 1–5 halogeno-$C_{1-4}$-alkylthio, $C_1$–$C_7$-alkylamino, $C_1$–$C_7$-dialkylamino, or in each case optionally substituted aryl, aralkyl, aryloxy or arylthio, or X and Y together with the adjoining C atoms form a carbocyclic ring which consists of 4 to 8 carbon atoms and which is optionally interrupted by at least one of nitrogen, oxygen and sulphur, and Z represents oxygen or $NOR^3$, where
$R^3$ represents hydrogen, or a straight-chain or branched radical selected from the group consisting of $C_1$–$C_7$-alkyl, $C_2$–$C_6$-alkenyl, $C_2$–$C_6$-alkynyl, $C_1$–$C_7$-halogenoalkyl having 1 to 15 identical or different halogen atoms, $C_2$–$C_6$-halogenoalkenyl having 1 to 11 identical or different halogen atoms, $C_2$–$C_6$-halogenoalkynyl having 1 to 9 identical or different halogen atoms, $C_3$–$C_6$-cycloalkyl, and optionally substituted phenyl or benzyl, the optional substituents on the aromatic radicals being selected from the group consisting of halogen, cyano, nitro, straight-chain or branched alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphonyl, alkylenedioxy and halogenoalkylenedioxy.

3. A substituted thieno[3,2-b]pyran-5,7-dione or tautomer thereof according to claim 1, in which
$R^1$ represents hydrogen, or a straight-chain or branched radical selected from the group consisting of $C_1$–$C_6$-alkyl, $C_3$–$C_4$-alkenyl, $C_3$–$C_4$-alkynyl, $C_1$–$C_4$-alkylsulphonyl, $C_1$–$C_4$-alkylcarbonyl, $C_2$–$C_5$-alkenylcarbonyl, and in each case optionally substituted phenyl, benzenesulphonyl, or benzoyl, $R^2$ represents a straight-chain or branched radical selected from the group consisting of $C_1$–$C_6$-alkyl, $C_1$–$C_4$-alkenyl, $C_2$–$C_4$-alkynyl, $C_1$–$C_6$-halogenoalkyl having 1 to 13 identical or different halogen atoms, $C_3$–$C_6$-cycloalkyl, and in each case optionally substituted phenyl, or benzyl, X and Y independently of one another represent hydrogen, halogen, cyano, nitro, straight-chain or branched $C_1$–$C_6$-alkyl, $C_2$–$C_5$-alkenyl, $C_2$–$C_5$-alkinyl, $C_1$–$C_6$-halogenoalkyl having 1 to 13 identical or different halogen atoms, $C_3$–$C_6$-cycloalkyl, $C_1$–$C_6$-alkylcarbonyl, $C_1$–$C_6$-alkyloxycarbonyl, $C_1$–$C_6$-alkyloxy, $C_1$–$C_6$-alkylthio, $C_1$–$C_6$-alkylamino, $C_1$–$C_6$-dialkylamino, or in each case optionally substituted aryl, aralkyl, aryloxy or arylthio, or X and Y together with the adjoining C atoms form a carbocyclic ring which consists of 4 to 8 carbon atoms and which is optionally interrupted by at least one of nitrogen, oxygen and sulphur, and Z represents oxygen or $NOR^3$, where
$R^3$ represents hydrogen, or a straight chain or branched alkyl radical selected from the group consisting of $C_1$–$C_6$-alkyl, $C_2$–$C_4$-alkenyl, $C_2$–$C_4$-alkynyl, $C_1$–$C_6$-halogenoalkyl having 1 to 13 identical or different halogen atoms, $C_2$–$C_4$-halogenoalkenyl having 1 to 7 identical or different halogen atoms, $C_2$–$C_4$-halogenoalkynyl having 1 to 5 identical or different halogen atoms $C_3$–$C_6$-cycloalkyl, and optionally substituted phenyl or benzyl, the optional substituents on the aromatic radicals being selected from the group consisting of halogen, cyano, nitro, straight-chain or branched $C_1$–$C_4$-alkyl, 1-5-halogeno-$C_{1-4}$-alkyl $C_{1-4}$-alkoxy, 1-5-halogeno-$C_{1-4}$-alkoxy, $C_{1-4}$-alkylthio, 1-5-halogeno-$C_{1-4}$-alkylthio, $C_{1-4}$-alkylsulphinyl, 1-5-halogeno-$C_{1-4}$-alkylsulphinyl, $C_{1-4}$-alkylsulphonyl, 1-5-halogeno-$C_{1-4}$-alkylsulphonyl, $C_{1-2}$-alkylenedioxy, and 1-4-halogeno-$C_{1-2}$-alkylenedioxy, or a salt thereof with a monovalent and divalent metal cation, or in each case optionally substituted ammonium ion, phosphonium ion, sulphonium ion or sulphoxonium ion.

4. A substituted thieno [3,2]pyran-5,7-dione or tautomer thereof according to claim 1, in which $R^1$ represents hydrogen, methyl, ethyl, n-propyl, i-propyl, n-butyl, i-butyl, t-butyl, n-pentyl, i-pentyl, allyl, n-butenyl, i-butenyl, propynyl, acetyl, propionyl, acroyl, isobutyryl, pivaloyl, valeroyl, phenyl, benzoyl, 4-methylbenzoyl, 4-ethylbenzoyl, 4-n-propylbenzoyl, 4-isopropylbenzoyl, 4-n-butylbenzoyl, 4-i-butylbenzoyl, 4-t-butylbenzoyl, 2,4,6-trimethylbenzoyl, p-methylphenylsulphonyl, or benzenesulfphonyl, $R^2$ represents methyl, ethyl, n-propyl, i-propyl, n-butyl, s-butyl, i-butyl, t-butyl, n-pentyl, i-pentyl, s-pentyl, t-pentyl, neo-pentyl, n-hexyl, cyclopropyl, cyclobutyl, cyclopentyl, cyclohexyl, or in each case optionally substituted phenyl or benzyl, X and Y independently of one another represent hydrogen, fluorine, chlorine, bromine, cyano, methyl, ethyl, n-propyl, isopropyl, n-butyl, i-butyl, s-butyl, t-butyl, n-pentyl, cyclopropyl, cyclobutyl, cyclopentyl, cyclohexyl, methoxy, ethoxy, n-propyloxy, i-propyloxy, n-butyloxy-, i-butyloxy, t-butyloxy, n-pentyloxy or neopentyloxy, methylthio-, ethylthio-, n-propylthio, i-propylthio, n-butylthio-, i-butylthio, t-butylthio, n-pentylthio, dimethylamino, diethylamino, dipropylamino, dibutylamino, methoxymethyl, ethoxymethyl, methylthiomethyl, ehtylthiomethyl, 1-methoxyethyl, 2-methoxythio-ethyl, 1,3-dimethoxypropyl, 2-ethoxy-ethyl, 1-methyl-2-methylthio-ethyl, 2-methyl-1-methylthiomethylpropyl, 1-methyl-butyl, 2-methyl-1-propenyl, phenyl, 4-methylphenyl, 4-trifluoromethylphenyl, 2,4-dichlorophenyl, 4-methoxyphenyl, 2,4,6-trimethylphenyl, 3.5-dibromophenyl, 4-methylthiophenyl or 4-fluorophenyl, or X and Y together with the adjoining C atoms form a carbocyclic ring which consists of 5 to 6 carbon atoms and which is optionally interrupted by at least one of nitrogen, oxygen and sulphur, and Z represents oxygen or $NOR^3$, where $R^3$ represents hydrogen, methyl, ethyl, n-propyl, i-propyl, n-n-butyl, i-butyl, t-butyl, allyl, prop-2-inyl, 3-fluoropropyl, trans-3-chloro-prop-2-inyl, 3-fluoropropyl, trans-3-chloro-prop-2-enyl, trans-but-2-enyl, cis-3-chloro-prop-2-enyl, but-2-inyl, 2-methoxyethyl, E-4(4-fluorophenyl)but-2-enyl, E-4(4-chlorophenyl)but-2-enyl, E-4(4-tert.-butylphenyl)but-2-enyl, E-4(4-trifluorophenyl)but-2-enyl, E-4-phenyl-but-2-enyl, 2-thienyl, 3-thienyl, 5-chloro-thienyl or optionally substituted benzyl, the optional substituents on the aromatic radicals being selected from the group consisting of halogen, cyano, nitro, methyl, ethyl, n-propyl, i-propyl, n-butyl, i-butyl, t-butyl, chloromethyl, fluoromethyl, dichloromethyl, trichloromethyl, difluormethyl, trifluoromethyl, trifluoromethoxy, trifluoromethylthio, methylsulphinyl, methylsulphonyl, trifluoromethylsulphinyl and trifluoromethylsulphonyl, or a salt thereof with sodium, potassium, or an equivalent of magnesium, calcium, manganese, copper, zinc and iron cations, or with an ammonium, phosphonium, sulphonium or sulphonium cation.

5. An endoparasiticidal or herbicidal composition comprising an endoparasiticidally or herbicidally effective amount of a compound according to claim 1 and a diluent.

6. A method of combating endoparasites or unwanted vegetation which comprises applying thereto or to a locus from which it is desired they be excluded an endoparasiticidally of herbicidally effective amount of a compound according to claim 1.

* * * * *

UNITED STATES PATENT AND TRADEMARK OFFICE
CERTIFICATE OF CORRECTION

PATENT NO. : 5,201,936
DATED : April 13, 1993
INVENTOR(S) : Bertram et al.

It is certified that error appears in the above-identified patent and that said Letters Patent is hereby corrected as shown below:

Col. 39, line 41     Before " represents " insert -- Z --

Col. 39, line 46     Delete "halogenoalkyenyl" and substitute -- halogenoalkenyl --

Col. 41, line 40     Delete " ehtylthiomethyl " and substitute -- ethylthiomethyl --

Col. 42, line 13     Delete " 3-fluoropropyl, trans-3-chloro-prop-2-inyl, "

Signed and Sealed this

First Day of March, 1994

Attest:

BRUCE LEHMAN

*Attesting Officer*     Commissioner of Patents and Trademarks